United States Patent
Mei et al.

(10) Patent No.: US 11,958,999 B2
(45) Date of Patent: Apr. 16, 2024

(54) LIGAND, LIGAND QUANTUM DOT, QUANTUM DOT LAYER AND METHOD FOR PATTERNING THE SAME

(71) Applicant: BOE TECHNOLOGY GROUP CO., LTD., Beijing (CN)

(72) Inventors: Wenhai Mei, Beijing (CN); Zhenqi Zhang, Beijing (CN); Aidi Zhang, Beijing (CN); Xiaoyuan Zhang, Beijing (CN); Haowei Wang, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 221 days.

(21) Appl. No.: 17/286,428

(22) PCT Filed: Sep. 11, 2020

(86) PCT No.: PCT/CN2020/114694
§ 371 (c)(1),
(2) Date: Apr. 16, 2021

(87) PCT Pub. No.: WO2021/063166
PCT Pub. Date: Apr. 8, 2021

(65) Prior Publication Data
US 2021/0388259 A1    Dec. 16, 2021

(30) Foreign Application Priority Data
Sep. 30, 2019  (CN) .......................... 201910939515.0

(51) Int. Cl.
| C09K 11/02 | (2006.01) |
| B82Y 20/00 | (2011.01) |
| B82Y 40/00 | (2011.01) |
| C07C 59/90 | (2006.01) |
| C09D 11/037 | (2014.01) |
| C09D 11/50 | (2014.01) |
| C09K 11/88 | (2006.01) |
| H10K 50/115 | (2023.01) |
| H10K 71/13 | (2023.01) |
| H10K 85/30 | (2023.01) |

(52) U.S. Cl.
CPC ............ *C09K 11/025* (2013.01); *C07C 59/90* (2013.01); *C09D 11/037* (2013.01); *C09D 11/50* (2013.01); *C09K 11/883* (2013.01); *H10K 85/381* (2023.02); *B82Y 20/00* (2013.01); *B82Y 40/00* (2013.01); *H10K 50/115* (2023.02); *H10K 71/13* (2023.02)

(58) Field of Classification Search
CPC ..... C09K 11/025; C07C 59/90; C09D 11/037; C09D 11/50; C09D 11/883; H10K 50/115; H10K 71/13
See application file for complete search history.

(56) References Cited

U.S. PATENT DOCUMENTS

| 11,453,820 | B2* | 9/2022 | Zhang ................. C09D 11/037 |
| 2018/0148638 | A1 | 5/2018 | Ahn et al. |
| 2018/0215695 | A1 | 8/2018 | Chen |
| 2020/0332181 | A1 | 10/2020 | Zhang |

FOREIGN PATENT DOCUMENTS

| CN | 106083573 A | 11/2016 |
| CN | 108102640 A | 6/2018 |
| CN | 108624320 A | 10/2018 |
| CN | 109863222 A | 6/2019 |
| CN | 109946924 A | 6/2019 |
| EP | 3327814 A1 | 5/2018 |
| IN | 109266350 A | 1/2019 |
| RU | 2689970 C1 | 5/2019 |

OTHER PUBLICATIONS

Wang et al., "Direct oxidative isoperfluoropropylation of terminal alkenes via hexafluoropropylene (HFP) and silver fluoride", Chem. Commun. 2018, 54, pp. 1877-1880, Jan. 19, 2018.*
First Office Action for Chinese Application No. 201910939515.0, dated Apr. 20, 2021, 9 pages.
International Search Report and Written Opinion for Application No. PCT/CN2020/114694, dated Dec. 2, 2020, 9 pages.
Kuhn et al., "Monoketals of 1.2 diketones. A contribution to the theory of the benzylic acid rearrangement" Chemische Berichte, Aug. 1961, pp. 2258-2263, vol. 94, Issue 8, https://doi.org/10.1002/cber.19610940849, 6 pages.
Bugakov et al., "Fluorescent thermostable crosslinked poly(dodecylmethacrylate) composites based on porous polyethylene abd CdSe/ZnS quantum dots," Polymer International, May 26, 2018, pp. 1275-1281, vol. 67, Issue 9, https://doi.org/10.1002/pi.5636, 7 pages.

* cited by examiner

*Primary Examiner* — C Melissa Koslow
(74) *Attorney, Agent, or Firm* — BROOKS KUSHMAN P.C.

(57) ABSTRACT

The present disclosure relates to a ligand for a quantum dot, a ligand quantum dot, a quantum dot layer and a method for patterning the same. The surface of the ligand quantum dot of the present disclosure is connected with the cleavage-type ligand including a first ligand unit A, a cleavage unit B, and an adhesion adjusting unit C. The method includes: providing a substrate; coating a mixture containing the ligand quantum dot on the substrate to form a quantum dot film; exposing a preset region of the quantum dot film to ultraviolet light, so that the cleavage unit B in the cleavage-type ligand undergoes a photolysis reaction, and a molecular segment containing the adhesion adjusting unit C and obtained after decomposition is detached from a surface of the quantum dot; and washing off an unexposed region of the quantum dot film with an organic solvent, followed by drying.

16 Claims, 2 Drawing Sheets

LIGAND, LIGAND QUANTUM DOT, QUANTUM DOT LAYER AND METHOD FOR PATTERNING THE SAME

CROSS-REFERENCE TO RELATED APPLICATIONS

This application is the U.S. national phase of PCT Application No. PCT/CN2020/114694 filed on Sep. 11, 2020, which claims priority to Chinese Patent Application No. 201910939515.0 filed on Sep. 30, 2019, which are incorporated herein by reference in their entireties.

TECHNICAL FIELD

The present disclosure relates to the field of display, in particular to a cleavage-type ligand for a quantum dot, a ligand quantum dot containing the cleavage-type ligand, a quantum dot layer, a method for patterning the same, as well as a light-emitting device and a display device containing the quantum dot layer.

BACKGROUND

With the continuous development of quantum dot preparation technology, the stability of the prepared quantum dots and the light-emitting efficiency of quantum dot light emitting devices prepared from the quantum dots are continuously improved. With the continuous development of research on the quantum dot light emitting diodes (QLED), the application prospect of a display device with a quantum dot light emitting diode in the display field is getting brighter. Theoretically, as compared with a conventional display device with an organic light emitting diode, a display device with a quantum dot light emitting diode has the advantages of better light source stability, longer life, wider color gamut, lower cost, and the like.

However, current display devices containing quantum dot light-emitting diodes have not yet reached the level of mass production, in which one of the important reasons is that the high-resolution patterning technology of quantum dot light emitting diodes has not yet made a breakthrough. The inorganic nanoparticle characteristics of quantum dots make it impossible for quantum dots to be formed as film by evaporation and patterned, and it is difficult to achieve higher resolution by inkjet printing.

SUMMARY

In one aspect, the present disclosure provides a cleavage-type ligand for quantum dots, having any one of the structures shown in the following Formulas I and V to IX:

A—B—C  (I)

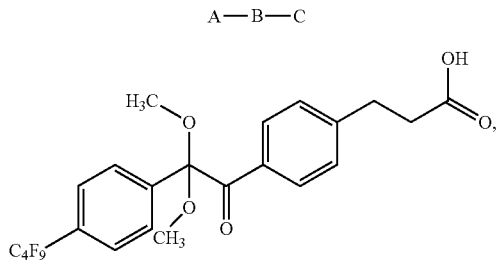

(V)

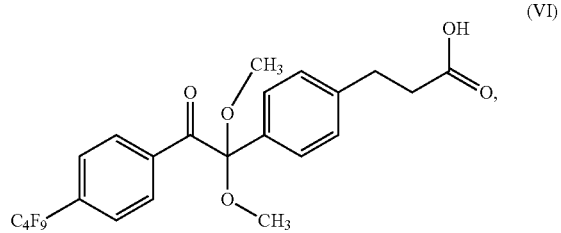

(VI)

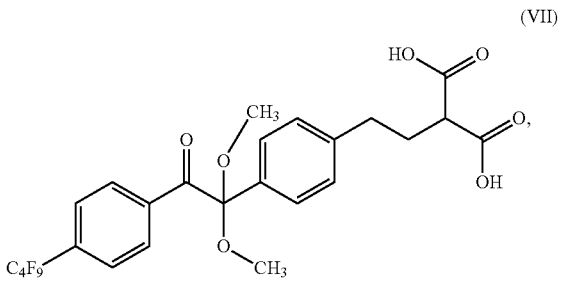

(VII)

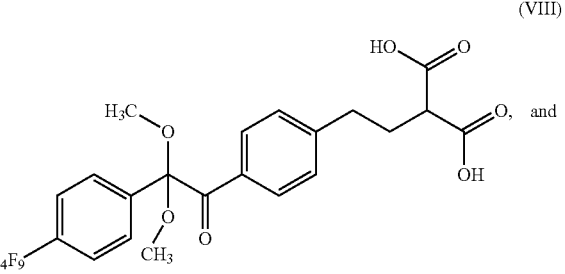

(VIII)

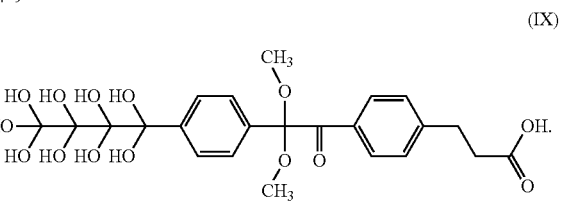

(IX)

in Formula I, A is a first ligand unit, B is a cleavage unit, and C is a adhesion adjusting unit; the first ligand unit A is at least one selected from mercapto, hydroxyl, amino, carboxyl, a phosphate group, a phosphate ester group, and a sulfonic group; the cleavage unit B is at least one selected from structures shown in the following Formulas III and IV:

  (III)

  (IV)

in the above Formulas III and IV, $R_5$, $R_6$, $R_7$ and $R_8$ are independently selected from alkylene and arylene; the adhesion adjusting unit C is at least one selected from a perfluoroalkyl group containing 3 or more carbon atoms, a group containing 3 or more hydrophilic functional groups, and a molecular chain containing 8 or more hydrophilic functional groups, and the hydrophilic functional groups includes hydroxyl, aldehyde group, an ester group and an ether group.

Optionally, $R_5$, $R_6$, $R_7$ and $R_8$ are independently selected from $C_1$ to $C_{12}$ alkylene and $C_6$ to $C_{12}$ arylene.

Optionally, the adhesion adjusting unit C is at least one selected from a perfluoroalkyl group containing 3 to 20 carbon atoms, a group containing 8 to 20 hydrophilic functional groups, and a molecular chain containing 8 to 20 hydrophilic functional groups.

Optionally, the adhesion adjusting unit C is $C_4F_9$ or $C_4(OH)_9$.

In another aspect, the present disclosure provides a ligand quantum dot, including the cleavage-type ligand of any one of the above items and a quantum dot.

Optionally, the ligand quantum dot further includes a soluble-type ligand connected to a surface of the quantum dot, in which the soluble-type ligand includes a second ligand unit and a $C_6$ to $C_{50}$ branched alkyl, and the second ligand unit is at least one selected from mercapto, hydroxyl, amino, carboxyl, a phosphate group, a phosphate ester group and a sulfonic group.

Optionally, the ligand quantum dot further includes a cross-linked type ligand connected to a surface of the quantum dot, in which the cross-linked type ligand includes a third ligand unit and a conjugated unit, the conjugated unit is a phenyl or a group having a conjugation effect and formed by connecting phenyl with a group containing a double bond or a triple bond, and the third ligand unit is at least one selected from mercapto, hydroxyl, amino, carboxyl, a phosphate group, a phosphate ester group and a sulfonic group.

Optionally, the group containing the double bond or the triple bond is at least one selected from alkenyl, alkynyl, an ester group, carbonyl, an aldehyde group, azido and cyano.

Optionally, the cleavage-type ligand has a mass accounting for 30% to 70% of a total mass of a ligand connected to a surface of the quantum dot, the soluble-type ligand and the cross-linked type ligand have a total mass accounting for 70% to 30% of a mass of all ligands connected to the surface of the quantum dot, and the cross-linked type ligand has a mass accounting for not greater than 40% of the total mass of the soluble-type ligand and the cross-linked type ligand.

In a yet aspect, the present disclosure provides a method for patterning a quantum dot layer, including: providing a substrate; coating a mixture containing the ligand quantum dot of any one of the above items on a surface of the substrate to form a quantum dot film, in which the adhesion adjusting unit C has a hydrophilic-hydrophobic property opposite to that of a surface of the substrate; exposing a preset region of the quantum dot film to ultraviolet light, so that the cleavage unit B in the cleavage-type ligand undergoes a photolysis reaction, and a molecular segment containing the adhesion adjusting unit C and obtained after decomposition is detached from a surface of the quantum dot; and washing an unexposed region of the quantum dot film with an organic solvent, followed by drying, to form a patterned quantum dot layer.

Optionally, the ligand quantum dot further includes a soluble-type ligand connected to a surface of the quantum dot, in which the soluble-type ligand includes a second ligand unit and a $C_6$ to $C_{50}$ branched alkyl, and the second ligand unit is at least one selected from mercapto, hydroxyl, amino, carboxyl, a phosphate group, a phosphate ester group and a sulfonic group.

Optionally, the ligand quantum dot further includes a cross-linked type ligand connected to a surface of the quantum dot, in which the cross-linked type ligand includes a third ligand unit and a conjugated unit, the conjugated unit is a phenyl or a group having a conjugation effect and formed by connecting phenyl with a group containing a double bond or a triple bond, and the third ligand unit is at least one selected from mercapto, hydroxyl, amino, carboxyl, a phosphate group, a phosphate ester group and a sulfonic group.

In a yet aspect, the present disclosure provides a quantum dot layer, including a quantum dot and a structure connected to a surface of the quantum dot and shown in Formula X:

$$A\text{-}B' \qquad (X)$$

in which A is a first ligand unit, and B' is a residual unit obtained after a cleavage unit is cleaved; the first coordination unit A is at least one selected from the group consisting of mercapto, hydroxyl, amino, carboxyl, a phosphate group, a phosphate ester group, and a sulfonic group; the residual unit has a structure shown below:

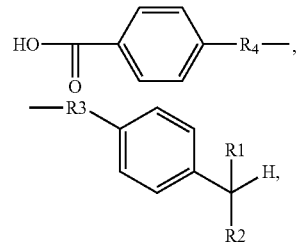

$-R_5-OH$, $-R_6-H$, $-R_7-OH$ or $-R_8-H$, in which $R_1$ and $R_2$ are independently selected from hydrogen, alkoxy, alkyl or aryl, and $R_3$ and $R_4$ are independently selected from alkylene and arylene.

In a yet aspect, the present disclosure provides a quantum dot light emitting device, including the above quantum dot layer.

In another aspect, the present disclosure provides a display device including the above quantum dot light emitting device.

DETAILED DESCRIPTION

Figure 1:
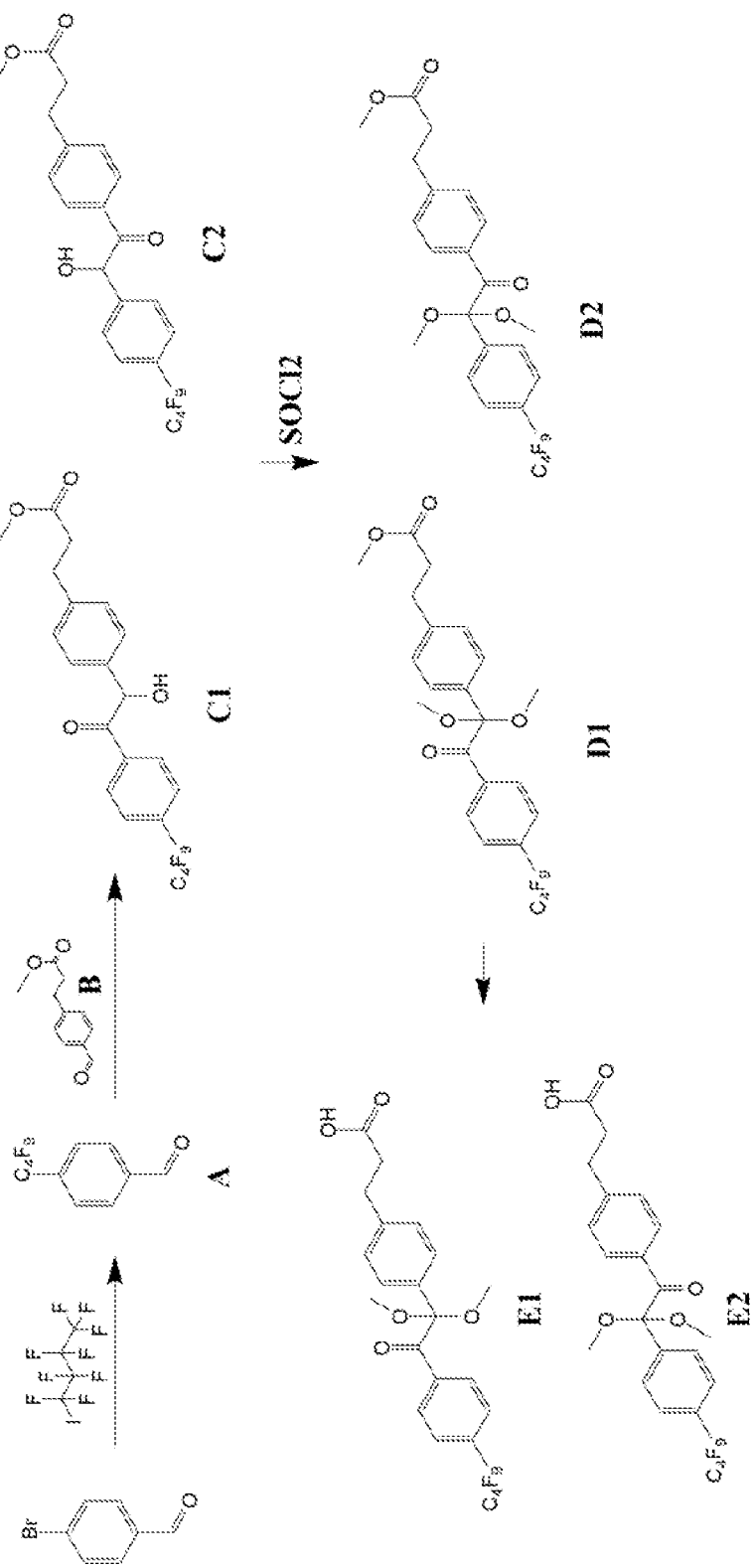
FIG. 1 is a flow chart for preparing the cleavage-type ligand shown by Formula I according to an embodiment of the present disclosure.

In order to make the objectives, the technical solutions, and the advantages of the examples of the present disclosure, the technical solutions in the embodiments of the present disclosure will be described clearly and completely hereinafter in conjunction with the drawings. Obviously, the following embodiments merely relate to a part of, rather than all of, the embodiments of the present disclosure. Based on these embodiments, a person skilled in the art may, without any creative effort, obtain the other embodiments, which also fall within the scope of the present disclosure.

The technical problem to be solved by the present disclosure is to provide a cleavage-type ligand for quantum dots, a ligand quantum dot containing the ligand, a quantum dot layer and a method for patterning the same, and the ligand or the ligand quantum dots is conducive the method to form a high-resolution quantum dot layer.

An embodiment of present disclosure provides a cleavage-type ligand for quantum dots, having any one of the structures shown in the following Formulas I and V to IX:

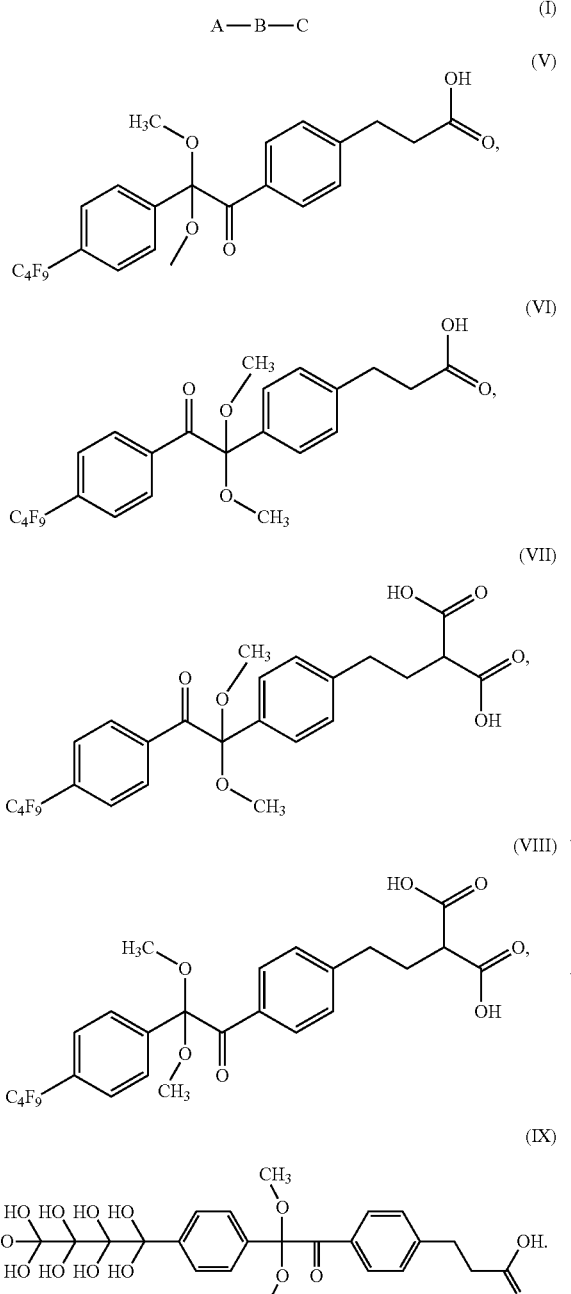

in Formula I, A is a first ligand unit, B is a cleavage unit, and C is a adhesion adjusting unit; the first ligand unit A is at least one selected from mercapto, hydroxyl, amino, carboxyl, a phosphate group, a phosphate ester group, and a sulfonic group; the cleavage unit B is at least one selected from structures shown in the following Formulas III and IV:

in which in the above Formulas III and IV, $R_5$, $R_6$, $R_7$ and $R_8$ are independently selected from alkylene and arylene; the adhesion adjusting unit C is at least one selected from a perfluoroalkyl group containing 3 or more carbon atoms, a group containing 3 or more hydrophilic functional groups, and a molecular chain containing 3 or more hydrophilic functional groups, and the hydrophilic functional groups includes hydroxyl, aldehyde group, an ester group and an ether group.

In an embodiment of the present disclosure, the cleavage-type ligand is connected to the quantum dot through the first ligand unit, the cleavage unit can be cleaved upon ultraviolet light irradiation, and the adhesion adjusting unit can adjust the adhesion between the quantum dot and the substrate. The first ligand unit, the cleavage unit and the adhesion adjusting unit are connected by chemical bonds or groups, and the specific connection mode is not specifically limited in the present disclosure. The ligand in the embodiments of the present disclosure can be used to prepare a high-resolution quantum dot layer.

Optionally, the adhesion adjusting unit C is at least one selected from a perfluoroalkyl group containing 3 to 20 carbon atoms, a group containing 8 to 20 hydrophilic functional groups, and a molecular chain containing 8 to 20 hydrophilic functional groups.

Optionally, $R_5$, $R_6$, $R_7$ and $R_8$ are independently selected from $C_1$ to $C_{12}$ alkylene and $C_6$ to $C_{12}$ arylene.

Optionally, the adhesion adjusting unit C is $C_4F_9$ or $C_4(OH)_9$.

Optionally, the first ligand unit is dicarboxyl. When a ligand containing dicarboxyl is coordinated with quantum dots, a stable ring structure can be formed, thereby forming stable ligand quantum dots.

According to an embodiment of the present disclosure, the cleavage-type ligand of the structure represented by Formula I is subjected to ultraviolet light irradiation, the light-sensitive chemical bond in the cleavage unit B is broken, and the adhesion unit C is detached from the ligand. For example, the ligand

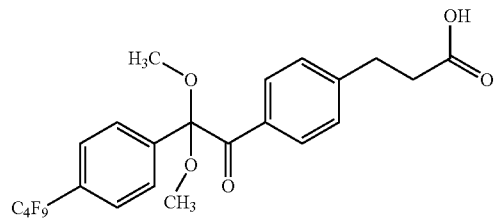

represented by Formula (V) undergoes a cleavage reaction after being subjected to the ultraviolet light irradiation, to form the structure shown below:

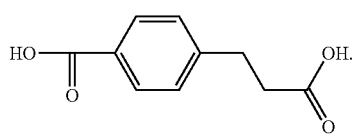 [SMILES: O=C(O)CCc1ccc(C(=O)O)cc1]

The cleavage-type ligand having the structure shown in Formula I in the embodiment of the present disclosure, such as the cleavage-type ligand shown in (V) or (VI), can be prepared according to the process shown in FIG. 1.

As shown in FIG. 1, taking the preparation of the ligands represented by Formula (V) and Formula (VI) as an example, the method for preparing the ligand represented by Formula I includes the following specific steps: bromobenzaldehyde and perfluoroiodobutane are mixed in a molar ratio of 1:1.1 and heated under reflux in tetrahydrofuran for 24 hours using cuprous iodide as a catalyst, and the crude product obtained is subjected to precipitation, extraction and column chromatography to obtain product A; A and B (p-(3-carboxymethyl-propyl)benzaldehyde) is dissolved in dimethyl sulfoxide (the solvent) in a molar ratio of 1:1, catalyzed by adding glacial acetic acid, and heated at 90° C. for 24 hours, and the crude product obtained is subjected to precipitation, extraction and column chromatography to obtain products C1 and C2; the mixture of C1 and C2 is dissolved in dimethyl sulfoxide, added with thionyl chloride and methanol, and stirred for 24 hours at room temperature, and the crude product obtained is subjected to precipitation, extraction and column chromatography to obtain products D1 and D2; and D1 and D2 are dissolved in tetrahydrofuran, added with potassium hydroxide and heated under reflux for 5 hours, to obtain product E1 (that is, the compound of Formula (VI)) and E2 (that is, the compound of Formula (V)).

In the ligand represented by Formula I of the present disclosure, if the adhesion adjusting unit is a perfluoroalkyl group containing 3 or more carbon atoms, the adhesion between the ligand and the surface of the hydrophilic substrate can be adversely affected due to the hydrophobicity of the perfluoroalkyl group containing 3 or more carbon atoms. After the adhesion adjusting unit is removed by cleavage, the adhesion between the ligand and the surface of the substrate is enhanced. If the adhesion regulating unit is a group containing 3 or more, or even more than 8 hydrophilic functional groups or a molecular chain containing more than 3, or even more than 8 hydrophilic functional groups, the adhesion between the ligand and the surface of the hydrophobic substrate may be adversely affected due to the hydrophobicity of the adhesion adjusting unit. After the adhesion adjusting unit is removed by cleavage, the adhesion between the ligand and the substrate layer is enhanced.

An embodiment of the present disclosure further provides a ligand quantum dot, including the cleavage-type ligand and quantum dot described in any of the above embodiments. The cleavage-type ligand is connected to the surface of the quantum dot through the ligand unit A.

Optionally, the ligand quantum dot further includes a soluble-type ligand connected to a surface of the quantum dot. Optionally, the soluble-type ligand includes a second ligand unit and a $C_6$ to $C_{50}$ branched alkyl. Optionally, the soluble-type ligand includes a $C_6$ to $C_{12}$ branched alkyl.

In the soluble-type ligand, the second coordination unit A is at least one selected from the group consisting of mercapto, hydroxyl, amino, carboxyl, a phosphate group, a phosphate ester group, and a sulfonic group. The soluble-type ligand can increase the solubility of quantum dots in organic solvents, so as to form a mixed solution containing quantum dots and easily form a high-resolution quantum dot film by coating.

The soluble-type ligand can be selected from

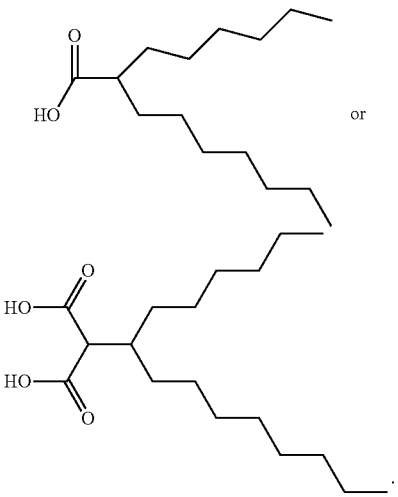

Optionally, the ligand quantum dot further includes a cross-linked type ligand connected to a surface of the quantum dot. Optionally, the cross-linked type ligand includes a third ligand unit and a conjugated unit, the conjugated unit is a phenyl or a group having a conjugation effect and formed by connecting phenyl with a group containing a double bond or a triple bond, and the third ligand unit is at least one selected from mercapto, hydroxyl, amino, carboxyl, a phosphate group, a phosphate ester group and a sulfonic group.

Optionally, the group containing the double bond or the triple bond is at least one selected from alkenyl, alkynyl, an ester group, carbonyl, an aldehyde group, azido and cyano.

The cross-linked type ligand may be selected from

Figure 2:
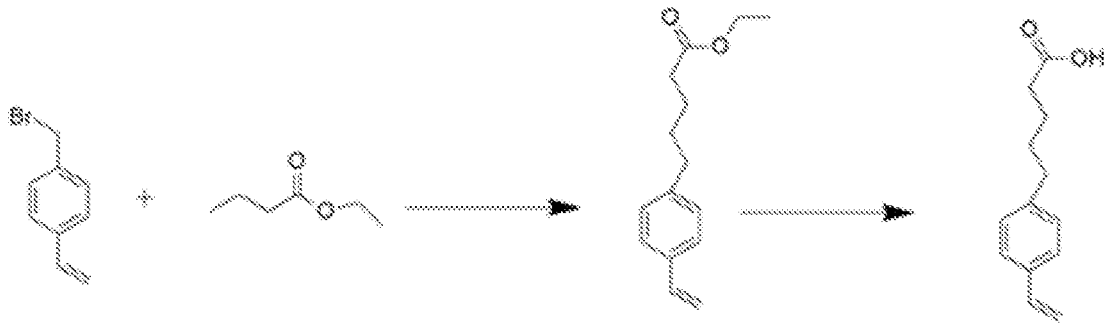
FIG. 2 is a flow chart for preparing a cross-linked type ligand according to an embodiment of the present disclosure.

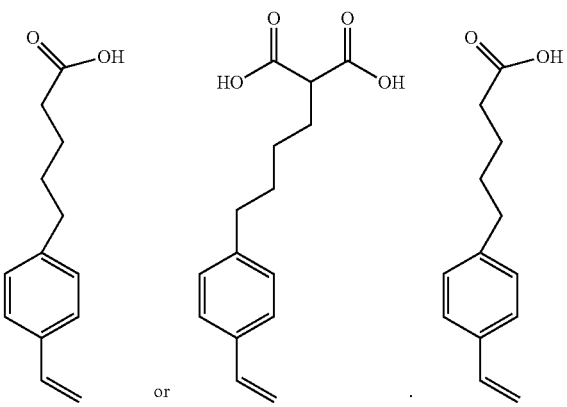 [SMILES: C=Cc1ccc(CCCCC(=O)O)cc1 ; C=Cc1ccc(CCCCC(C(=O)O)C(=O)O)cc1 ; C=Cc1ccc(CCCCC(=O)O)cc1]

can be prepared according to the process shown in FIG. 2.

The cross-linked type ligand can undergo a self-cross-linking reaction after being subjected to the ultraviolet light irradiation, so as to reduce the solubility of the quantum dots in the organic solvent, so that the quantum dots are difficult to be washed away by the organic solvent.

Optionally, the cleavage-type ligand represented by the general Formula I has a mass accounting for 30% to 70% of a total mass of all ligands connected to a surface of the quantum dot, and the soluble-type ligand and the cross-linked type ligand have a total mass accounting for 70% to 30% of a total mass of all ligands connected to the surface of the quantum dot. Optionally, the cross-linked type ligand has a mass accounting for not greater than 40% of the total mass of the soluble-type ligand and the cross-linked type ligand. When the ligand in the above mass range is selected, the solubility of the quantum dot in the organic solvent can be ensured, and the properties can change after the quantum dot is subjected to the ultraviolet light irradiation.

The ligand represented by Formula I, the soluble-type ligand, and the cross-linked-type ligand according to the present disclosure can be connected to the surface of the quantum dot through ligand exchange.

Figure 3:
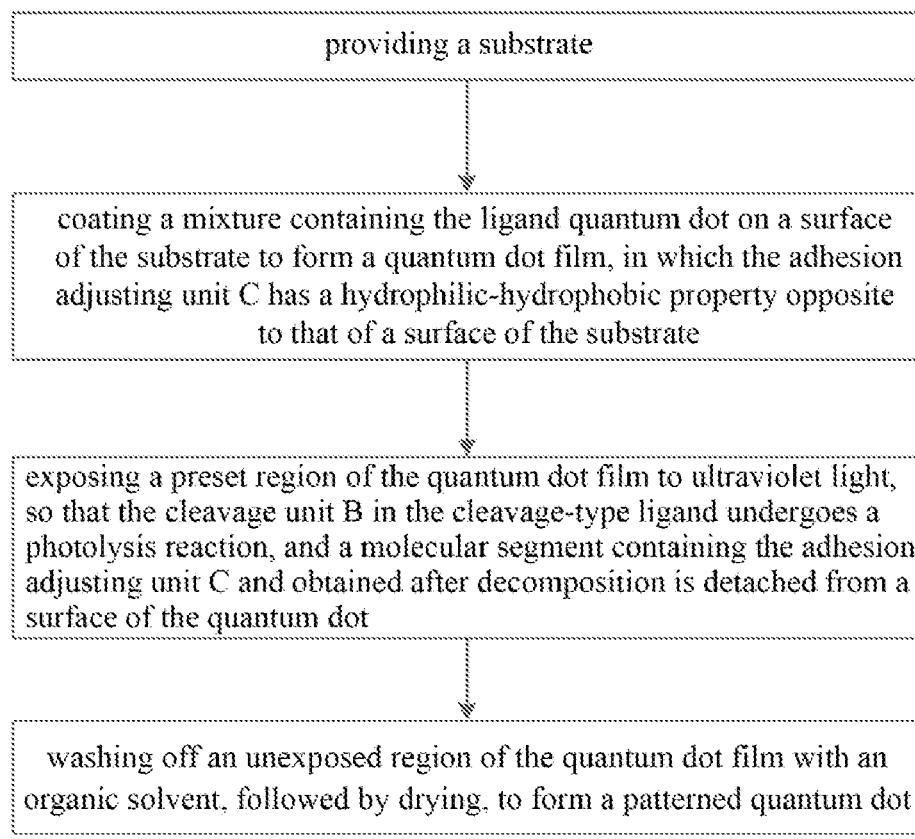
FIG. 3 is a flow chart of a method for patterning a quantum dot layer according to an embodiment of the present disclosure.

An embodiment of the present disclosure further discloses a method for patterning the quantum dot layer. As shown in FIG. 3, the method specifically includes the following steps: providing a substrate; coating a mixture containing the ligand quantum dot of any one of the above embodiments on the substrate to form a quantum dot film, in which the adhesion adjusting unit C has a hydrophilic-hydrophobic property opposite to that of a surface of the substrate; exposing a preset region of the quantum dot film to ultraviolet light, so that the cleavage unit B in the cleavage-type ligand undergoes a photolysis reaction, and a molecular segment containing the adhesion adjusting unit C and obtained after decomposition is detached from a surface of the quantum dot; and washing an unexposed region of the quantum dot film with an organic solvent, followed by drying, to form a patterned quantum dot layer.

In the embodiment of the present disclosure, the cleavage-type unit in the ligand in the preset region undergoes a photolysis reaction through ultraviolet light exposure treatment, and a molecular segment containing the adhesion adjusting unit and obtained after decomposition is detached from a surface of the quantum dot. This reduces the solubility of the quantum dots, and it is difficult to remove the quantum dots during subsequent washing with the organic solvent. Moreover, the adhesion between the ligand obtained after irradiation cleavage and the surface of the substrate to which it is attached is enhanced, so that the quantum dots in the preset region are better retained. The quantum dots in the non-exposed region are easily removed during washing with the organic solvent. Moreover, the adhesion adjusting unit affects the adhesion between the ligand and the surface of the substrate to which it is attached, so the quantum dot layer in the non-exposed region is more easily eluted. Therefore, a high-resolution patterned quantum dot layer is easily formed according to the method of the present disclosure.

The method for patterning the quantum dot layer will be described in detail in conjunction with the following specific steps S1 to S4.

Step S1: providing a substrate.

Optionally, the substrate may be an organic substrate, or an inorganic substrate, such as zinc oxide and nickel oxide. Optionally, the surface of the substrate may be hydrophilic or hydrophobic. If a QLED is prepared by the method of the present disclosure, the substrate may be a hole injection layer or a hole transport layer.

Step S2: coating a mixture containing the ligand quantum dot of any one of the above embodiments on the substrate to form a quantum dot. Optionally, when the adhesion adjusting unit C has a hydrophilic property, the surface of the substrate has a hydrophobic property; or when the adhesion adjusting unit C has a hydrophobic property, the surface of the substrate has a hydrophilic property.

In the present disclosure, the hydrophilic property means that the contact angle of the object to water is less than 90 degrees, and the hydrophobic property refers to the contact angle of the object to water is greater than 90 degrees. The difference between the contact angle of the adhesion adjusting unit and the substrate to water is at least 15 degrees. When the adhesion adjusting unit is hydrophilic, the substrate is made of a hydrophobic material; and when the adhesion adjusting unit is hydrophobic, the substrate is made of a hydrophilic material.

Optionally, the ligand quantum dot further includes a soluble-type ligand connected to a surface of the quantum dot. Optionally, the soluble-type ligand includes a second ligand unit and a $C_6$ to $C_{50}$ branched alkyl. Optionally, the soluble ligand includes a second ligand unit and a $C_6$ to $C_{12}$ branched alkyl. Optionally, the third coordination unit A is at least one selected from the group consisting of mercapto, hydroxyl, amino, carboxyl, a phosphate group, a phosphate ester group, and a sulfonic group.

The mixture containing the ligand quantum dots is a mixture of a ligand quantum dot and an organic solvent. If the soluble-type ligand is further connected to the surface of the quantum dot, the quantum dot is easily dissolved in an organic solvent.

Optionally, the ligand quantum dot further includes a cross-linked type ligand connected to a surface of the quantum dot. Optionally, the cross-linked type ligand includes a third ligand unit and a conjugate unit. Optionally, the conjugated unit is a phenyl or a group having a conjugation effect and formed by connecting phenyl with a group containing a double bond or a triple bond. Optionally, the third coordination unit A is at least one selected from the group consisting of mercapto, hydroxyl, amino, carboxyl, a phosphate group, a phosphate ester group, and a sulfonic group.

Optionally, the cleavage-type ligand represented by the general Formula I has a mass accounting for 30% to 70% of a total mass of all ligands connected to a surface of the quantum dot. Optionally, the soluble-type ligand and the cross-linked type ligand have a total mass accounting for 70% to 30% of a total mass of all ligands connected to the surface of the quantum dot. Optionally, the cross-linked type ligand has a mass accounting for not greater than 40% of the total mass of the soluble-type ligand and the cross-linked type ligand.

Step S3: exposing a preset region of the quantum dot film to ultraviolet light, so that the cleavage unit B in the cleavage-type ligand undergoes a photolysis reaction, and a molecular segment containing the adhesion adjusting unit C and obtained after decomposition is detached from a surface of the quantum dot.

After the quantum dot in the preset region is exposed to light, the ligand represented by Formula I and connected to the surface of the quantum dot undergoes a photolysis reaction, and a molecular segment containing the adhesion adjusting unit is detached from a surface of the quantum dot. After the photolysis reaction, the adhesion between the ligand quantum dot and the surface of the substrate is relatively strong. A ligand represented by Formula I is connected to a surface of an unexposed region of the quantum dot. Since the difference in the hydrophilicity between the adhesion adjusting unit and the surface of the substrate is relatively large, the adhesion between the quantum dot and the surface of the substrate is relatively weak. Therefore, the adhesion between the quantum dot film in the preset region and the surface of the substrate is far greater than the adhesion between an unexposed region of the quantum dot film and the surface of the substrate.

If a cross-linked type ligand is connected to the surface of the quantum dot, the cross-linked ligand will undergo a free radical cross-linking reaction after being exposed to ultraviolet light, to form a self-crosslinked polymer. This reduces the solubility of the quantum dot in the organic solvent, thereby making it difficult for the quantum dot to be washed off by an organic solvent. Optionally, the wavelength of the ultraviolet light is in a range from 365 to 436 nm.

Step S4: washing an unexposed region of the quantum dot film with an organic solvent, followed by drying, to form a patterned quantum dot.

Since the adhesion between the unexposed region of the quantum dot and the substrate is weak, the unexposed region of the quantum dot can be removed by washing with an organic solvent, and the removal efficiency is high. In the preset region, the length of the molecular chain of the cleavage-type ligand shown in Formula I and connected to the surface of the quantum dot changes significantly after the photolysis reaction, and the cross-linked type ligand connected to the surface of the quantum dot forms a self-crosslinking polymer by exposure. These two aspects work together to reduce the solubility of the quantum dot in the organic solvent, and it is difficult to be washed off by the organic solvent.

Optionally, the drying is treated at a temperature from 110 to 120° C. for a time period in a range from 20 to 25 minutes to remove the organic solvent.

An embodiment of the present disclosure further provides quantum dot layer, including a quantum dot and a structure connected to a surface of the quantum dot and shown in Formula X:

A-B' (X)

in which A is a first ligand unit, and B' is a residual unit obtained after a cleavage unit is cleaved; the first coordination unit A is at least one selected from the group consisting of mercapto, hydroxyl, amino, carboxyl, a phosphate group, a phosphate ester group, and a sulfonic group; the residual unit has a structure shown below:

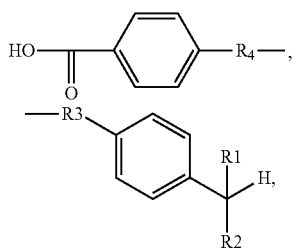

—$R_5$—OH, —$R_6$—H, —$R_7$—OH or —$R_8$—H, in which $R_1$ and $R_2$ are independently selected from hydrogen, alkoxy, alkyl or aryl, and $R_3$, $R_4$, $R_5$, $R_6$, $R_7$ and $R_8$ are independently selected from alkylene and arylene.

The residual unit is a group of the cleavage unit represented by Formula I that is subjected to a cleavage reaction through ultraviolet light irradiation and left on the surface of the quantum dot.

In a yet aspect, the present disclosure provides a quantum dot light emitting device, including the above quantum dot layer. Optionally, the quantum dot light emitting device may be a quantum-dot light emitting diode. The quantum-dot light emitting diode includes a cathode, an electron injection layer, an electron transport layer, a quantum dot layer, a hole transport layer, a hole injection layer and an anode, which are arranged in sequence.

An embodiment of the present disclosure further provides a display device, including the above quantum dot light emitting device.

EXAMPLE

In order to further understand the technical solutions of the present disclosure, the quantum dot and the method for patterning the quantum dot layer of the present disclosure will be described in detail below in conjunction with specific embodiments. The protection scope of the present disclosure is not limited by the following specific Examples.

Example 1

Quantum dots are CdSe/ZnS green quantum dots, in which the compound

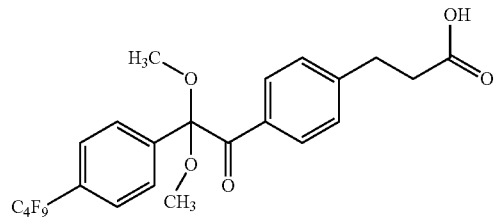

is the cleavage-type ligand, the compound

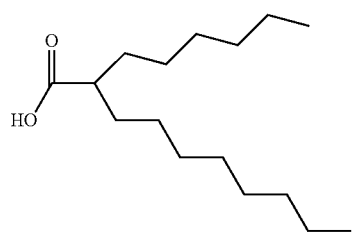 [SMILES: CCCCCCCCC(CCCCCC)C(=O)O]

is the soluble-type ligands, and the compound

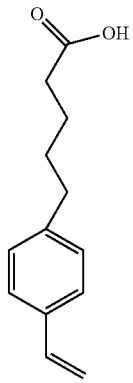

is the cross-linked type ligand.

Based on the total mass of all ligands connected to the surface of the quantum dot, the mixed ligand including 50% of the first ligand, 25% of the soluble-type ligand, and 25% of the cross-linked type ligand exchanges ligand with the original oleic acid ligand on the quantum dot, to prepare the ligand quantum dot according to this example.

A Merck organic film (purchased from Merck) was spin-coated with a mixed solution containing the above quantum dots, to form a quantum dot film. The quantum dot film was irradiated with 365 nm ultraviolet light. The quantum dot film after the exposure treatment is washed with a mixed solution of p-xylene and heptane. Then, it was treated at 120° C. for 20 minutes. The patterned green quantum dot layer of this example was prepared.

After testing the surface, the ligand quantum dots prepared from the ligands according to the present disclosure or the quantum-dot display device prepared from the ligand quantum dot prepared from the ligand according to the present disclosure has a higher resolution.

The description of the above Examples is merely used for helping to understand the technical solutions of the present disclosure and inventive concepts thereof. It should be noted that a person skilled in the art may make further improvements and modifications to the disclosure without departing from the principle/spirit of the present disclosure, and these improvements and modifications shall also fall within the scope of the present disclosure.

What is claimed is:

1. A cleavage-type ligand for quantum dots, having any one of structures shown in the following Formulas I and V to IX:

A—B—C (I)

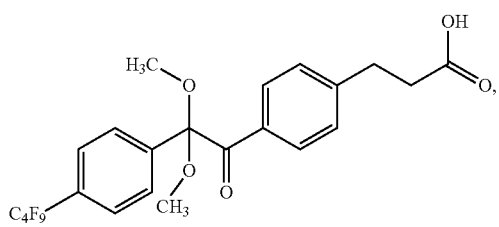
(V)

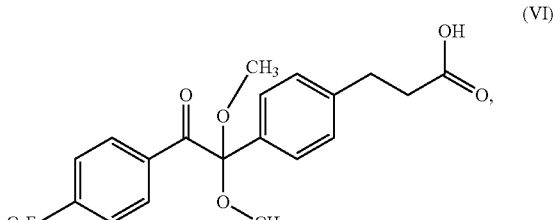
(VI)

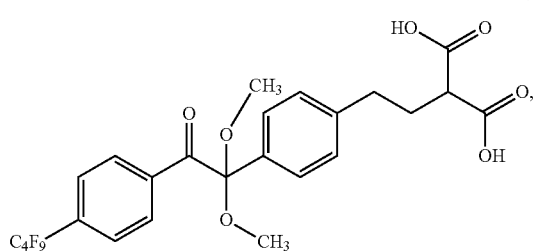
(VII)

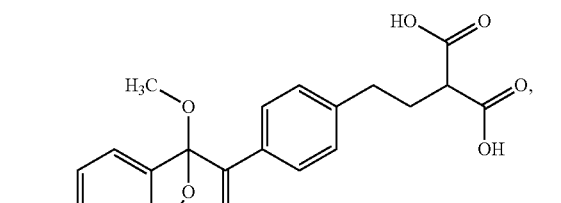
(VIII)

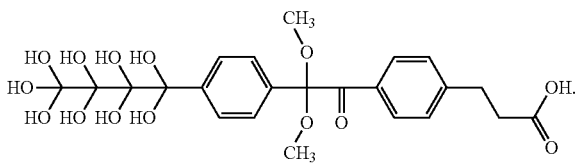
(IX)

wherein in Formula I, A is a first ligand unit, B is a cleavage unit, and C is an adhesion adjusting unit;
wherein the first ligand unit A is at least one selected from mercapto, hydroxyl, amino, carboxyl, a phosphate group, a phosphate ester group, and a sulfonic group;
wherein the cleavage unit B is at least one selected from structures shown in the following Formulas III and IV:

(III)

(IV)

in the above Formulas III and IV, $R_5$, $R_6$, $R_7$ and $R_8$ are independently selected from alkylene and arylene;
wherein the adhesion adjusting unit C is at least one selected from a perfluoroalkyl group containing 4 or more carbon atoms, a group containing 3 or more hydrophilic functional groups, and a molecular chain containing 3 or more hydrophilic functional groups, and the hydrophilic functional groups comprises hydroxyl, aldehyde group, an ester group and an ether group.

2. The cleavage-type ligand of claim 1, wherein $R_5$, $R_6$, $R_7$ and $R_8$ are independently selected from $C_1$ to $C_{12}$ alkylene and $C_6$ to $C_{12}$ arylene.

3. The cleavage-type ligand of claim 1, wherein the adhesion adjusting unit C is at least one selected from a perfluoroalkyl group containing 4 to 20 carbon atoms, a group containing 8 to 20 hydrophilic functional groups, and a molecular chain containing 8 to 20 hydrophilic functional groups.

4. The cleavage-type ligand of claim 3, wherein the adhesion adjusting unit C is $C_4F_9$ or $C_4(OH)_9$.

5. A ligand quantum dot, comprising the cleavage-type ligand of claim 1 and a quantum dot.

6. The ligand quantum dot of claim 5, wherein the ligand quantum dot further comprises a soluble-type ligand connected to a surface of the quantum dot,
wherein the soluble-type ligand comprises a second ligand unit and a $C_6$ to $C_{50}$ branched alkyl, and the second ligand unit is at least one selected from mercapto, hydroxyl, amino, carboxyl, a phosphate group, a phosphate ester group and a sulfonic group.

7. The ligand quantum dot of claim 6, wherein the ligand quantum dot further comprises a cross-linked type ligand connected to a surface of the quantum dot, wherein the cross-linked type ligand comprises a third ligand unit and a conjugated unit, the conjugated unit is a phenyl or a group having a conjugation effect and formed by connecting phenyl with a group containing a double bond or a triple bond, and the third ligand unit is at least one selected from mercapto, hydroxyl, amino, carboxyl, a phosphate group, a phosphate ester group and a sulfonic group.

8. The ligand quantum dot of claim 7, wherein the group containing the double bond or the triple bond is at least one selected from alkenyl, alkynyl, an ester group, carbonyl, an aldehyde group, azido and cyano.

9. The ligand quantum dot of claim 7, wherein the cleavage-type ligand has a mass accounting for 30% to 70% of a total mass of a ligand connected to a surface of the quantum dot, the soluble-type ligand and the cross-linked type ligand have a total mass accounting for 30% to 70% of a total mass of all ligands connected to the surface of the quantum dot, and the cross-linked type ligand has a mass accounting for not greater than 40% of the total mass of the soluble-type ligand and the cross-linked type ligand.

10. The ligand quantum dot of claim 5, wherein $R_5$, $R_6$, $R_7$ and $R_8$ are independently selected from $C_1$ to $C_{12}$ alkylene and $C_6$ to $C_{12}$ arylene.

11. The ligand quantum dot of claim 5, wherein the adhesion adjusting unit C is at least one selected from a perfluoroalkyl group containing 4 to 20 carbon atoms, a group containing 8 to 20 hydrophilic functional groups, and a molecular chain containing 8 to 20 hydrophilic functional groups.

12. A method for patterning a quantum dot layer, comprising:

providing a substrate;

coating a mixture containing the ligand quantum dot of claim 6 on the substrate to form a quantum dot film, wherein the adhesion adjusting unit C has a hydrophilic-hydrophobic property opposite to that of a surface of the substrate;

exposing a preset region of the quantum dot film to ultraviolet light, so that the cleavage unit B in the cleavage-type ligand undergoes a photolysis reaction, and a molecular segment containing the adhesion adjusting unit C and obtained after decomposition is detached from a surface of the quantum dot; and washing off an unexposed region of the quantum dot film with an organic solvent, followed by drying, to form a patterned quantum dot layer.

13. The method of claim 12, wherein the ligand quantum dot further comprises a soluble-type ligand connected to a surface of the quantum dot, wherein the soluble-type ligand comprises a second ligand unit and a $C_6$ to $C_{50}$ branched alkyl, and the second ligand unit is at least one selected from mercapto, hydroxyl, amino, carboxyl, a phosphate group, a phosphate ester group and a sulfonic group.

14. The method of claim 13, wherein the ligand quantum dot further comprises a cross-linked type ligand connected to a surface of the quantum dot, wherein the cross-linked type ligand comprises a third ligand unit and a conjugated unit, the conjugated unit is a phenyl or a group having a conjugation effect and formed by connecting phenyl with a group containing a double bond or a triple bond, and the third ligand unit is at least one selected from mercapto, hydroxyl, amino, carboxyl, a phosphate group, a phosphate ester group and a sulfonic group.

15. The method of claim 14, wherein the group containing the double bond or the triple bond is at least one selected from alkenyl, alkynyl, an ester group, carbonyl, an aldehyde group, azido and cyano.

16. The method of claim 14, wherein the cleavage-type ligand has a mass accounting for 30% to 70% of a total mass of a ligand connected to a surface of the quantum dot, the soluble-type ligand and the cross-linked type ligand have a total mass accounting for 30% to 70% of a total mass of all ligands connected to the surface of the quantum dot, and the cross-linked type ligand has a mass accounting for not greater than 40% of the total mass of the soluble-type ligand and the cross-linked type ligand.

\* \* \* \* \*